(12) United States Patent
Singh et al.

(10) Patent No.: US 10,155,717 B2
(45) Date of Patent: Dec. 18, 2018

(54) SOLID, HETEROGENEOUS CATALYSTS AND METHODS OF USE

(71) Applicant: SBI BioEnergy, Edmonton (CA)

(72) Inventors: Inder Pal Singh, Edmonton (CA); Shradha Singh, Edmonton (CA); Ritesh Patel, Burnaby (CA); Bharat Mistry, Edmonton (CA); Manish Mehta, Edmonton (CA); Peter Omolo Otieno, Edmonton (CA)

(73) Assignee: SBI BioEnergy, Edmonton, AB (CA)

( * ) Notice: Subject to any disclaimer, the term of this patent is extended or adjusted under 35 U.S.C. 154(b) by 178 days.

(21) Appl. No.: 15/063,141

(22) Filed: Mar. 7, 2016

(65) Prior Publication Data

US 2016/0185706 A1 Jun. 30, 2016

Related U.S. Application Data

(62) Division of application No. 13/059,932, filed as application No. PCT/CA2009/001165 on Aug. 20, 2009, now Pat. No. 9,278,340.

(60) Provisional application No. 61/090,781, filed on Aug. 21, 2008.

(51) Int. Cl.

| | | |
|---|---|---|
| *C07C 67/03* | (2006.01) | |
| *C07C 67/08* | (2006.01) | |
| *C07C 69/52* | (2006.01) | |
| *C07C 69/24* | (2006.01) | |
| *B01J 23/00* | (2006.01) | |
| *B01J 23/10* | (2006.01) | |
| *B01J 27/26* | (2006.01) | |
| *B01J 29/06* | (2006.01) | |
| *B01J 29/70* | (2006.01) | |
| *B01J 35/00* | (2006.01) | |
| *B01J 37/00* | (2006.01) | |
| *B01J 37/03* | (2006.01) | |
| *C07B 41/12* | (2006.01) | |
| *C10L 1/02* | (2006.01) | |
| *C11C 3/00* | (2006.01) | |
| *B01J 29/072* | (2006.01) | |
| *B01J 29/076* | (2006.01) | |
| *C11C 3/10* | (2006.01) | |

(52) U.S. Cl.
CPC ............ *C07C 67/08* (2013.01); *B01J 23/002* (2013.01); *B01J 23/10* (2013.01); *B01J 27/26* (2013.01); *B01J 29/06* (2013.01); *B01J 29/072* (2013.01); *B01J 29/076* (2013.01); *B01J 29/7003* (2013.01); *B01J 29/7053* (2013.01); *B01J 35/0006* (2013.01); *B01J 37/0009* (2013.01); *B01J 37/03* (2013.01); *C07B 41/12* (2013.01); *C07C 67/03* (2013.01); *C07C 69/24* (2013.01); *C07C 69/52* (2013.01); *C10L 1/026* (2013.01); *C11C 3/003* (2013.01); *C11C 3/10* (2013.01); *B01J 2229/42* (2013.01); *B01J 2523/00* (2013.01); *B01J 2523/23* (2013.01); *B01J 2523/27* (2013.01); *B01J 2523/31* (2013.01); *B01J 2523/3706* (2013.01); *C10G 2300/1011* (2013.01); *C10L 2200/0476* (2013.01); *C10L 2270/026* (2013.01); *Y02E 50/13* (2013.01); *Y02P 30/20* (2015.11)

(58) Field of Classification Search
CPC ......... C07B 41/12; C07C 67/03; C07C 67/08; C07C 69/52; C07C 69/24; B01J 2523/27; B01J 2523/3706; B01J 2523/23; B01J 2523/31; C11C 3/003; C10L 1/026; C10L 2270/026; C10L 2270/0476; C10G 2300/1011
USPC .......................... 554/167, 170; 560/103, 111
See application file for complete search history.

(56) References Cited

U.S. PATENT DOCUMENTS

| | | |
|---|---|---|
| 3,816,342 A | 6/1974 | Plank et al. |
| 3,899,310 A | 8/1975 | Chi et al. |
| 4,992,613 A | 2/1991 | Brownscombe |
| 5,053,372 A | 10/1991 | Brownscombe |
| 5,194,244 A | 3/1993 | Brownscombe et al. |
| 5,439,859 A | 8/1995 | Durante et al. |
| 7,151,187 B2 | 12/2006 | Delfort et al. |
| 2005/0032628 A1 | 2/2005 | Collier et al. |
| 2005/0119112 A1 | 6/2005 | Pfenninger et al. |
| 2005/0205464 A1 | 9/2005 | Hu et al. |
| 2007/0066838 A1 | 3/2007 | Hillion et al. |
| 2007/0093380 A1 | 4/2007 | Srinivas et al. |
| 2008/0008639 A1 | 1/2008 | Sakurai et al. |
| 2008/0114181 A1 | 5/2008 | Banavali et al. |

OTHER PUBLICATIONS

Lopez, "Heterofeneous Catalysis and Biodiesel Forming Reactions", (2007), all Dissertations, paper 121, pp. 1-196.*
Brito et al., "Zeolite Y as a Heterogeneous Catalyst in Biodiesel Fuel Production from Used Vegetable Oil", Energy & Fuels, 2007, nn21, pp. 3280-3283.*

* cited by examiner

*Primary Examiner* — Elizabeth D Wood
(74) *Attorney, Agent, or Firm* — Norton Rose Fulbright LLP

(57) ABSTRACT

Solid mixed catalysts and methods for use in conversion of triglycerides and free fatty acids to biodiesel are described. A batch or continuous process may be used with the catalysts for transesterification of triglycerides with an alkyl alcohol to produce corresponding mono carboxylic acid esters and glycerol in high yields and purity. Similarly, alkyl and aryl carboxylic acids and free fatty acids are also converted to corresponding alkyl esters. The described catalysts are thermostable, long lasting, and highly active.

18 Claims, No Drawings

SOLID, HETEROGENEOUS CATALYSTS AND METHODS OF USE

CROSS REFERENCE TO RELATED APPLICATIONS

This application is a divisional of U.S. patent application Ser. No. 13/059,932, entitled "SOLID, HETEROGENEOUS CATALYSTS AND METHODS OF USE," filed Apr. 12, 2011, and issued as U.S. Pat. No. 9,278,340, which is the national phase under 35 U.S.C. § 371 of PCT International Application No. PCT/CA2009/001165 with an International Filing Date of Aug. 20, 2009, which claims the priority of U.S. Provisional Patent Application No. 61/090,781 filed Aug. 21, 2008, all of which are incorporated by reference herein, in their entirety.

FIELD OF THE INVENTION

The present invention relates generally to the production of biodiesel from triglycerides and free fatty acids. More particularly, the present invention relates to solid, heterogeneous catalysts for use in the production of biodiesel.

BACKGROUND OF THE INVENTION

Biodiesel is a non-toxic fuel that may be used alone or blended with petroleum diesel at any ratio to create a biodiesel blend. Biodiesel has a high octane number, is essentially free of sulfur and aromatics, and is therefore a clean burning fuel, free of NOx and SOx.

Biodiesel is commonly produced by transesterification, the reaction of an alcohol with triglycerides present in animal fat or vegetable oil. Generally, such reactions are catalyzed by homogeneous catalysts such as mineral acids, metal hydroxide, metal alkoxides, and carbonates. As mineral acid catalyzed reactions are slow and therefore economically non-viable, metal hydroxides such as sodium or potassium hydroxides are more commonly used as they are relatively inexpensive and suitably effective. One disadvantage to using alkaline hydroxides or carbonates in transesterification reactions is the generation of soap as a reaction byproduct. The generation of soap compromises product yields and product quality. Glycerol (glycerine) is also produced as a byproduct, however the presence of water and soaps creates an emulsion that complicates the purification of biodiesel and the separation of glycerol from the fatty acid esters. Generally, copious amounts of acids and water are used to neutralize catalyst and remove soaps from the desirable reaction products. As a result, the increased number of steps required to obtain purified biodiesel and useable quality glycerol add tremendously to the cost of production, and also lead to a certain degree of environmental pollution.

The following equations illustrate the reactions that take place during transesterification to biodiesel by existing methods, using homogeneous catalysts.

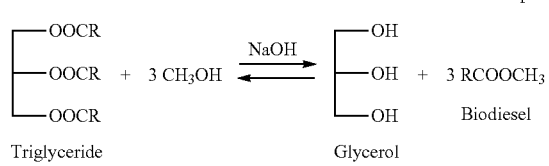

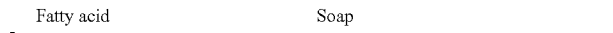

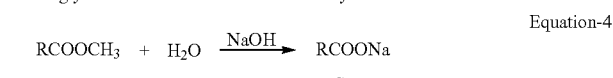

Further attempts have been made in the prior art to replace homogeneous catalysts with solid catalysts. Such replacement of homogeneous catalysts, for example with solid metal oxides and double metal cyanides, is perceived to have the advantages of simple retrieval of catalyst, elimination of soap formation and reduction of environmental pollutants. Further, the use of solid catalysts in place of homogeneous catalysts may lead to higher-quality esters and glycerol, which are more easily separable and without added cost to refine the resulting ester (see for example U.S. Pat. No. 6,147,196 to Stern et al). In accordance with this expectation, a number of solid catalysts have now been reported in literature. These are generally based on metal oxides and double metal cyanides to affect the desired transesterification reaction shown in equation-5 below.

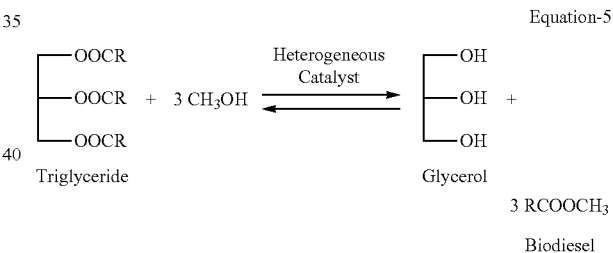

European patent EP-80-198-243 describes a solid, heterogeneous catalyst that is based on a mixture of iron oxide with alumina. This catalyst requires a very large catalyst to oil ratio, and extended contact time of more than 6 hours. Reaction temperatures of 280° C. to 320° C. are typically required, which results in coloration of the biodiesel and presence of impurities.

U.S. Pat. No. 5,908,946 describes catalysts prepared from mixtures of zinc oxide, and alumina zinc aluminate. While the catalyst does provide complete conversion to methyl ester, long reaction times and high temperatures are required. Moreover, the reaction is sensitive to water and free fatty acids. When free fatty acid conversion is desired, an esterification step must be carried out prior to the transesterification reaction.

U.S. Pat. No. 7,151,187 describes catalysts made by combining two or more of titanium isopropoxide, zinc oxide, alumina, and bismuth salts using nitric acid. Use of nitric acid is not desirable, as it is corrosive, toxic, and has a negative impact on the environment. Further, the use of nitric acid also impacts the basicity of the catalyst, which may affect the transesterification reaction.

It has further been shown that exchange of sodium ions in the 4 Å molecular sieves (formula: $Na_{12}[(AlO_2)_{12}(SiO_2)_{12}].xH_2O$), with either $K^+$ or $Cs^+$ leads to a material with higher basicity which is essential in heterogeneous transesterification catalysis. However, testing has shown that despite enhancement of the basic sites, these ion-exchanged zeolites failed to achieve complete transformation of triglycerides to biodiesel.

A double metal cyanide (DMC) catalyst-$Fe_2Zn_3(CN)_{10}$ has also been shown to transesterify oils at relatively lower temperatures. However, the slow pace of reaction leads to extended reaction time and requires excessive catalyst and reactor volume.

A suitable heterogeneous catalyst and method for complete transformation of triglycerides to biodiesel and for conversion of free fatty acids to corresponding esters has not been described to date. Further, such reactions do not appear to be currently possible under mild temperature and pressure conditions, while minimizing reaction time and product purification steps.

SUMMARY

In accordance with a first aspect of the invention, there is provided a solid, heterogeneous catalyst preparation for use in an esterification or transesterification reaction, the mixed catalyst preparation comprising at least one molecular sieve and at least one catalyst, wherein the catalyst comprises a metal oxide or double-metal cyanide.

In an embodiment, the metal oxide is aluminum oxide, calcium oxide, gallium oxide, hafnium oxide, iron oxide, lanthanum oxide, silicon oxide, strontium oxide, titanium oxide, zinc oxide, or zirconium oxide. The metal oxide may be formed by calcination of a metal hydroxide, for example, aluminum hydroxide, calcium hydroxide, gallium hydroxide, hafnium hydroxide, iron hydroxide, lanthanum hydroxide, silicon hydroxide, strontium hydroxide, titanium hydroxide, zinc hydroxide, or zirconium hydroxide.

In an embodiment, the double-metal cyanide (DMC) is of the general formula $Fe_2M_3(CN)_{10}$ wherein M is lanthanum, zinc, copper or aluminum.

In suitable embodiments, the molecular sieve may be of the type 3 Å, 4 Å, or 5 Å, having the general formula $K_nNa_{(12-n)}[(AlO_2)_{12}(SiO_2)_{12}].xH_2O$, $Na_{12}[(AlO_2)_{12}(SiO_2)_{12}].xH_2O)$ or $Ca_nNa_{(12-n)}[(AlO_2)_{12}(SiO_2)_{12}].xH_2O$, respectively. The molecular sieve may be, for example, a natural or synthetic zeolite. Preferably, the molecular sieve is a modified molecular sieve (MMS), modified to enhance the basicity of the molecular sieve.

Suitable modified molecular sieves (MMS) may have been modified to replace at least one sodium ion within the molecular sieve with at least one metal cation. Suitable metal cations include $K^+$, $Cs^+$, and the like, resulting in a general formula of $K_nNa_{(12-n)}[(AlO_2)_{12}(SiO_2)_{12}].xH_2O$, $K_mCa_nNa_{\{12(m+2n)\}}[(AlO_2)_{12}(SiO_2)_{12}].xH_2O$, $Cs_nNa_{(12-n)}[(AlO_2)_{12}(SiO_2)_{12}].xH_2O$, or $Cs_mCa_nNa_{\{12-(m+2n)\}}[(AlO_2)_{12}(SiO_2)_{12}].xH_2O$, for example.

In various embodiments, any of the catalyst preparations may be provided in powdered, pelleted, extruded, and/or calcined form. The catalyst remains heterogeneous during the reaction, and is generally recoverable from the reaction products by filtration.

In accordance with a second aspect of the invention, there is provided a catalyst of the molecular formula: $x(La_2O_3).y(La(OH)_3).z(TiO_2)$ wherein x, y and z independently have a value between 1-2. Such catalyst may be prepared from lanthanum oxide or lanthanum hydroxide and titanium oxide, and these oxides may be prepared in situ.

In accordance with a third aspect of the invention, there is provided a modified molecular sieve (MMS) of the general formula $K_nNa_{(12-n)}[(AlO_2)_{12}(SiO_2)_{12}].xH_2O$, $K_mCa_nNa_{\{12(m+2n)\}}[(AlO_2)_{12}(SiO_2)_{12}].xH_2O$, $Cs_nNa_{(12-n)}[(AlO_2)_{12}(SiO_2)_{12}].xH_2O$, or $CsmCa_nNa_{\{12-(m+2n)\}}[(AlO_2)_{12}(SiO_2)_{12}].xH_2O$.

In accordance with a fourth aspect of the invention, there is provided a catalyst according to the formula $a(La_2O_3).x(TiO_2).y(ZnO).z(MMS)$, wherein A and X are each 1; Y is 1-2, Z is 3-4, and wherein MMS is a modified molecular sieve of the general formula $K_nNa_{(12-n)}[(AlO_2)_{12}(SiO_2)_{12}].xH_2O$, $K_mCa_nNa_{\{12(m+2n)\}}[(AlO_2)_{12}(SiO_2)_{12}].xH_2O$, $Cs_nNa_{(12-n)}[(AlO_2)_{12}(SiO_2)_{12}].xH_2O$, or $Cs_mCa_nNa_{\{12-(m+2)\}}[(AlO_2)_{12}(SiO_2)_{12}].xH_2O$.

In accordance with a fifth aspect of the invention, there is provided a catalyst according to the formula $(AlO_3).(TiO_2).(ZnO).z(MMS)$ wherein z is 1-10 and wherein MMS is a modified molecular sieve of the general formula $K_nNa_{(12-n)}[(AlO_2)_{12}(SiO_2)_{12}].xH_2O$, $K_mCa_nNa_{\{12(m+2n)\}}[(AlO_2)_{12}(SiO_2)_{12}].xH_2O$, $Cs_nNa_{(12-n)}[(AlO_2)_{12}(SiO_2)_{12}].xH_2O$, or $Cs_mCa_nNa_{\{12-(m+2n)\}}[(AlO_2)_{12}(SiO_2)_{12}].xH_2O$.

In accordance with a sixth aspect of the invention, there is provided a catalyst according to the formula $\{(Fe_2M_3(CN)_{10}\}.Al_2O_3.TiO_2.ZnO.MMS$, wherein M is Cu, Al or La, and wherein MMS is a molecular sieve of the general formula $K_nNa_{(12-n)}[(AlO_2)_{12}(SiO_2)_{12}].xH_2O$, $K_mCa_nNa_{\{12(+2n)\}}[(AlO_2)_{12}(SiO_2)_{12}].xH_2O$, $Cs_nNa_{(12-n)}[(AlO_2)_{12}(SiO_2)_{12}].xH_2O$, or $Cs_mCa_nNa_{\{12-(m+2n)\}}[(AlO_2)_{12}(SiO_2)_{12}].xH_2O$.

In accordance with another aspect of the invention, there is provided a method for effecting esterification or transesterification of a starting material, comprising reacting the starting material with an alcohol in the presence of a solid, heterogeneous catalyst as described above.

The starting material may be an oil, and/or may comprise triglycerides, diglycerides, monoglycerides, free fatty acids, carboxylic acids and/or a mixture thereof. The method may be used to produce biodiesel and/or glycerol as a reaction product. Notably, in suitable embodiments, soap is not produced as a byproduct of the reaction.

In an embodiment, the reaction is conducted at temperatures between 150° C. and 250° C. Further, the reaction may be conducted at pressures less than 1000 psi. In various embodiments, the reaction may be conducted in a batch reactor or continuous reactor such as a fixed bed reactor. The reaction may be conducted in two or more successive stages. In a fixed bed reactor, the reaction may be conducted with a ratio of 0.1-2.0 volumes of injected oil/volume of catalyst per hour.

DESCRIPTION

Generally, the present invention provides solid, heterogeneous catalyst formulations and methods for use in the production of alkyl esters from a starting material containing any one or more of the following: triglycerides, diglycerides, monoglycerides, free fatty acids, or a mixture thereof, and aromatic carboxylic acids, aliphatic carboxylic acids.

The terms "oil", "feedstock", and "starting material" as used herein refer to a substance having any detectable triglycerides, diglycerides, monoglycerides and/or free fatty acid and/or carboxylic acid (whether aromatic or aliphatic) content, such as animal fats, vegetable oils, used cooking oils, and the like. Examples of vegetable oils include, without limitation, canola oil, corn oil, soybean oil, palm oil, coconut oil, jatropha oil, camelina oil, cottonseed oil, flax seed oil, sunflower oil, tall oil and rapeseed oil. Examples of animal fats include, without limitation, beef tallow, pork lard, and the like. Other further starting materials may also be appropriate, such as glycerides present in or obtained from certain types of algae, etc.

The term "heterogeneous" as used herein with respect to solid catalysts, refers to any solid physical form of suitable catalyst, whether a catalyst is calcined or otherwise hardened, whether provided in powder, pellet, balled, or extruded form or anchored to a solid structure such as a molecular sieve or natural or synthetic solid state composition. Such catalysts are generally not solubilized during the reaction and the majority of the catalyst is recoverable from the reaction products by simple filtration.

Catalyst and Reaction Overview

Notably, the catalysts and methods may be used in the production of high yield, high purity biodiesel. Generally, the catalyst may be a metal oxide, or double metal cyanide, or mixtures of the foregoing. The catalysts are provided in solid form, for example in powdered, pelleted, or extruded form, supported on a solid structure such as a molecular sieve. The resulting catalysts are thermostable. For example, the metal oxide based catalysts described below are stable above 600° C., maintain a high level of activity even after prolonged use, provide excellent selectivity, and are insoluble in triglycerides and alkyl alcohols, preventing elution and volume loss. Further, these catalysts are not usually limited by reaction temperature and are highly tolerant of free fatty acids and water content during use.

Equations describing the general reactions are represented below in Equations 6 through 8.

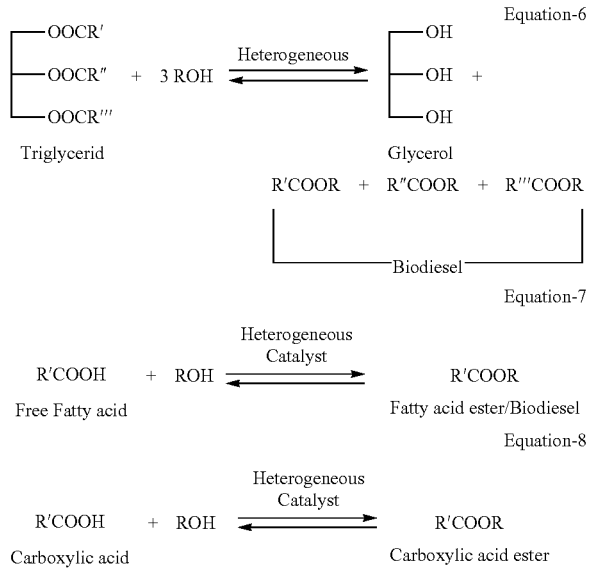

In the above equations, R', R", and R'" may be the same or different, and each may be a $C_1$ to $C_{22}$ linear or branched chain alkyl group, which may be further substituted with hydroxyl, alkoxy or halogens like chloro, bromo or fluoro or an aryl group that can be substituted with chloro, bromo, fluoro, nitro, lower alkoxy or lower alkyl such as methyl, ethyl, propyl, isopropyl or butyl which may be further substituted with halogens such as chloro, bromo, fluoro or a phenyl group that can be substituted with chloro, bromo, fluoro nitro, lower alkyl or alkoxy group. Further, each may represent an alkyl group of a monocarboxylic acid such as acetic, propionic, butyric, caproic, caprilic, capric, lauric, myristic, palmitic, oleic, stearic or a dicarboxylic acid such as adipic acid, which are in an ester form with a $C_1$ to $C_{18}$ monohydric aliphatic alcohol such as methyl, ethyl, propyl, isopropyl, butyl and stearyl alcohol, a monohydric aromatic alcohol such as benzyl or substituted benzyl alcohol or a dihydric alcohol such as ethylene glycol, propylene glycol, butane diol or a polyhydric alcohol such as glycerol, sorbitol, polyerythritol, polyethylene glycol and poly propylene glycol etc.

Further, ROH in equations 6 through 8 represents suitable alcohols, including without limitation: a $C_1$ to $C_{18}$ monohydric aliphatic alcohol such as methanol, ethanol, propanol, isopropanol, butyl alcohol, and stearyl alcohol; a monohydric aromatic alcohol such as benzyl alcohol or a substituted benzyl alcohol; a dihydric alcohol such as ethylene glycol, propylene glycol, and butanediol; or a polyhydric alcohol such as glycerol, sorbitol, polyerythritol, polyethylene glycol, and polypropylene glycol. Other suitable alcohols may also be used, as will be apparent to those of skill in the art.

Metal Oxide Catalysts

In equations 6 through 8, the catalyst may include an oxide of a metal, for example aluminum, calcium, cerium, gallium, hafnium, iron, lanthanum, magnesium, strontium, titanium, zirconium, or zinc. Such metal oxides or hydroxides may be used alone or in combination with similar or dissimilar catalysts, and the catalyst is provided in solid form. For example, the catalyst may be supported on a molecular sieve or zeolite, in which some of the sodium ions have been exchanged for potassium or cesium ions. The catalysts may be provided as a powder, pellets, balls, or extruded forms, and calcined under vacuum or in the presence of a neutral gas (such as argon, nitrogen, or helium) at temperatures between 200° C. to 1200° C., usually between 400° C. to 800° C. Such oxides may be obtained commercially or prepared from appropriate metal halide, hydroxide, or a metal nitrate.

Double Metal Cyanide Catalysts

In equations 6 through 8, the catalyst may include a double metal cyanide of the general formula $Fe_2M_3(CN)_n(ROH).xM_2.yH_2O)$, where M is a metal, for example lanthanum, strontium, copper, aluminum, magnesium cobalt and titanium. Values for x and y may range between 1 and 2. Such catalysts may be used alone or in combination with similar catalysts or with the above-described metal oxide/hydroxide catalysts, with the catalyst provided in solid form. For example, the catalyst may be supported on a molecular sieve or zeolite, in which some of the sodium ions have been exchanged for potassium or cesium ions. The catalysts may be provided as a powder, pellets, balls, or extruded forms, and calcined in the presence or absence of a neutral gas (such as argon, nitrogen, or helium) at temperatures between 100° C. to 200° C., usually between 160° C. to 180° C.

Use of Molecular Sieves in Catalyst Preparation

The mixed catalyst may include a molecular sieve, for example a natural or synthetic zeolite. Such substances may vary in composition and crystal structure. The catalyst may, for example, be a titanium zeolite prepared by exchange of silicon atoms with titanium atoms. Further, the molecular sieves may by of types 3 Å, 4 Å, and 5 Å. For example, type 3 Å of formula $K_nNa_{12-n}[(AlO_2)_{12}(SiO_2)_{12}].xH_2O$, or type 4 Å of formula $Na_{12}[(AlO_2)_{12}(SiO_2)_{12}].xH_2O$, where n and x are integers. The molecular sieve is first treated to exchange one or more of the existing sodium ions with potassium and cesium ions to produce enhanced basic sites.

The resulting substance may be calcined in the presence or absence of a neutral gas (such as nitrogen, argon, or helium) and may be used alone as a catalyst or as a solid support for the metal oxide/hydroxide and double metal cyanide catalysts described above.

Reaction Methods

The above-described catalysts may be used with equal efficiency in a batch, intermittent/semi continuous, or continuous mode at temperatures between 160° C. and 225° C. and pressures up to 1000 psi, depending on the specific catalyst, starting material, and process chosen.

Fatty acid esters and glycerol products from the reactor are generally of high purity, and the glycerol is colorless and high in quality. Quality of the reaction products may be further improved by treatment with activated charcoal, resin, or clay, or by distillation. Any remaining monoglycerides in the ester phase may be removed with the glycerol layer by partial evaporation of alcohol from the reaction mixture.

Batch mode example: Generally, for batch mode reaction, a mixture of alkyl alcohol, oil, and a catalyst is placed in a sealed autoclave and exposed to temperatures between 150° C. and 300° C., typically between 180° C. and 230° C. for 30 to 120 minutes. The ratio of catalyst to oil should be 1-10% by weight, and typically 2-6% by weight. The alcohol ratio should be 1-10 volume equivalents, typically 3-8 volume equivalents, most suitably 6 equivalents with respect to the amount of oil present. After cooling and depressurizing, the reaction mixture is recovered from the autoclave and filtered to remove the catalyst, which may be stored for later reuse. Excess alcohol is recovered by distillation, and the alkyl ester product is recovered from residue by decanting the separated glycerol.

Continuous/fixed bed example: Generally, oil and alcohol are fed at predetermined fixed rates into a continuous fixed bed reactor containing the desired catalyst formulation. The reactor is maintained at a temperature of 160° C. to 300° C., typically 180° C. to 230° C. depending on the catalyst used. Typical variables should be considered, including type and quality of feedstock, nature of alcohol, molar ratio of alcohol to oil, reaction time, temperature, pressure, and nature and quantity of catalyst.

Catalysts—Examples

All reagents and alcohols used in the following examples were of technical grade. The triglyceride source/starting material was food grade canola oil with approximately 1% free fatty acids. All metal oxides, molecular sieves, and carboxylic acids were purchased from Aldrich Chemical Co. For free fatty acid reactions, hydrolyzed canola and safflower oils were used as a source of free fatty acids. Reactions were followed by thin layer chromatography and 400 MHz NMR. GC analyses were performed following ASTM protocols on HP 6890 gas chromatograph.

Preparation of MMS-4 ÅK

Potassium exchanged modified molecular sieves were prepared by partial ion exchanging molecular sieves of molecular formula, $Na_{12}[(AlO_2)_{12}(SiO_2)_{12}]\cdot xH_2O$ (MS-4 Å). 800 g of MS-4 Å were suspended in 5000 ml, 0.5 Molar aqueous solution of potassium hydroxide and heated under reflux for 5 h and allowed to cool to room temp. The exchanged molecular sieves were washed repeatedly to remove excess potassium hydroxide from the molecular cages of the sieves.

Preparation of MS-4 ÅCs

Cesium exchanged modified molecular sieves were prepared by partial ion exchanging molecular sieves of molecular formula, $Na_{12}[(AlO_2)_{12}(SiO_2)_{12}]\cdot xH_2O$ (MS-4 Å). MS-4 Å (100 g) was suspended in 700 ml, 0.5 Molar aqueous solution of cesium chloride and heated under reflux for 5 h and allowed to cool to room temp. The exchanged molecular sieves were washed repeatedly to remove excess cesium chloride from the molecular cages of the sieves.

Preparation of MS-5 ÅK

Potassium and cesium exchanged modified molecular sieves were prepared by partial ion exchanging molecular sieves molecular formula, $Ca_nNa_{12-2n}[(AlO_2)_{12}(SiO_2)_{12}]\cdot xH_2O$. MS-5 Å (100 g) was suspended in 7000 ml, 0.5 Molar aqueous solution of cesium chloride and heated under reflux for 5 h and allowed to cool to room temp. The exchanged molecular sieves were washed repeatedly to remove excess cesium chloride from the molecular cages of the sieves.

Preparation of MS-5 ÅCs

Cesium exchanged modified molecular sieves were prepared by partial ion exchanging molecular sieves of molecular formula, $Ca_nNa_{12-2n}[(AlO_2)_{12}(SiO_2)_{12}]\cdot xH_2O$. MS-5 Å (100 g) was suspended in 700 ml, 0.5 Molar aqueous solution of cesium chloride and heated under reflux for 5 h and allowed to cool to room temp. The exchanged molecular sieves were washed repeatedly to remove excess cesium chloride from the molecular cages of the sieves.

Preparation of Catalyst C-I

Lanthanum chloride heptahydrate (25 g) was dissolved in water (100 ml) at room temperature and a mixture of a solution of potassium hydroxide (1M) and potassium carbonate (250 ml) was added over 1 h, whereupon a white precipitate was formed. Resulting suspension was further stirred for 1 hr; the solid was filtered, rinsed with 3×50 ml of 1:1 methanol water mixture. The resulting solid was dried at 100° C. for 24 h and calcined at 600° C. for 3 hours to get lanthanum oxide (Catalyst C-I).

Preparation of Catalyst C-II

Lanthanum chloride heptahydrate (15.2 g) in water (100 ml) was added to a solution of calcium chloride (30 g) in water (150 ml) at room temperature under vigorous stirring. A mixture of a solution of potassium hydroxide (1M, 200 ml) and potassium carbonate (0.5 M, 1000 ml) was added under stirring over one hour, whereby a white precipitate is obtained. Reaction mixture was further stirred for one hour then filtered to recover a white solid, washed with 3×50 ml of 1:1 methanol:water mixture. Solid was dried at 100° C. for 24 h and then calcined at 600° C. for 3 hours to obtain lanthanum calcium oxide, $x(La_2O_3)\cdot y(CaO)$ (where x=1 and y=3), hereinafter referred to as catalyst C-II.

Preparation of Catalyst C-III

Lanthanum aluminum oxide, $x(La_2O_3)\cdot y(Al_2O_3)$ (where x=2 and y=1) hereinafter referred to as catalyst C-III was prepared following the procedure described catalyst C-II using aluminum chloride (17 g) and lanthanum chloride (25 g).

Preparation of Catalyst C-IV

Lanthanum zinc oxide, $x(La_2O_3)\cdot y(ZnO)$ (where x=2 and y=1) hereinafter referred to as catalyst C-IV was prepared following the procedure described catalyst C-II using zinc chloride (17 g) and lanthanum chloride (25 g).

Catalysts C-V to C-XIV

Catalysts C-V to C-XIV were prepared by mixing required metal oxides and exchanged or un-exchanged molecular sieves from Table-1, respectively in water to make a paste. The paste was extruded, dried at 100° C. for 24 h and calcined at 600° C. for 3 hours to obtain Catalysts from C-V to C-XIV (Table-1).

TABLE 1

Preparation of mixed metal oxide catalysts:

| Catalyst | $Al_2O_3$ (g) | ZnO (g) | $TiO_2$ (g) | $La_2O_3$ (g) | $La_2O_3 \cdot TiO_2$ (g) | $Fe_3O_4$ (g) | Water (ml) | MMS-4ÅK (g) | MMS-5ÅK (g) | Yield (g) |
|---|---|---|---|---|---|---|---|---|---|---|
| C-V    | 6.0  |      |      | 9.8  |      |      |       | 11.5  |      | 25.2 |
| C-VI   | 2.3  |      |      | 4.6  |      |      | 8.0   | 2.3   |      | 8.9  |
| C-VII  | 8.0  | 16.0 | 16.0 |      |      |      | 30.0  | 30.0  |      | 65.0 |
| C-VIII | 30.0 | 30.0 | 30.0 |      |      |      | 200.0 | 250.0 |      | 295  |
| C-IX   |      |      |      |      | 30.2 |      |       |       |      | 29.7 |
| C-X    |      | 18.0 |      |      | 18.0 |      | 40.0  | 30.0  |      | 60.0 |
| C-XI   | 4.5  |      |      |      | 9.0  |      | 20.0  | 10.5  |      | 22.8 |
| C-XII  |      |      |      |      |      | 20.0 |       |       |      | 20.0 |
| C-XIII | 3.0  | 3.0  | 3.0  |      |      | 6.0  | 40.0  | 25.0  |      | 37.5 |
| C-XIV  | 3.6  | 8.2  | 8.2  |      |      |      | 25    |       | 13.4 | 32.8 |

Preparation of Catalyst C-XV

An aqueous solution of ammonium hydroxide (4 ml) was added drop wise into a stirred solution of 1.3 g of aluminum chloride dissolved in 5 ml of deionized water. To the resulting white suspension, a solution of zinc oxide (0.9 g) in a solution of nitric acid (2.5 g) and water (7.5 Å ml) was added and stirred to get a clear solution. This clear solution was absorbed on 3 molecular sieves of molecular formula, $K_nNa_{12-n}[(AlO_2)_{12}(SiO_2)_{12}] \cdot xH_2O$, (Ms-3 Å, 30 g) for one hour and then dried at 100° C. for 5 hours. To this material at RT was added ammonium hydroxide solution (2 ml) and dried at 100° C. for 5 hours. The material was calcined at 600° C. for 3 hours to give catalyst C-XV.

Preparation of Catalyst C-XVI

A solution of potassium hexacyanoferrate(II)-trihydrate (7.4 g, 17.5 mmol) in 50 ml of water was added to lanthanum chloride heptahydrate (65.1 g) dissolved in a mixture of water (50 ml) and t-butanol (20 ml) at 50° C. over one hour. Reaction mixture was further stirred for additional 18 h and cooled to ambient temperature. Separated solid was filtered, washed with a 3×40 ml of 1:1 mixture of water and t-butanol. It was dried at RT overnight, then at 60° C. under reduced pressure for 5 h and finally at 170° C. for another 5 h to a constant weight. Dried material having molecular formula $Fe_2La_3(CN)_{10}$, herein referred to as catalyst C-XVI.

Preparation of Catalyst C-XVII

DMC catalyst C-XVII having molecular formula $Fe_2Cu_3(CN)_{10}$ was prepared using hexacyanoferrate(II)-trihydrate (7.4 g) and copper(II)sulfate (55.9 g) following the method described for catalyst C-XVI.

Preparation of Catalyst C-XVIII

DMC catalyst C-XVIII having molecular formula $Fe_2Al_3(CN)_{10}$ was prepared using hexacyanoferrate(II)-trihydrate (7.4 g) and aluminum chloride (23.3 g) following the method described for catalyst C-XVI.

Preparation of Catalysts C-XIX to C-XXI

Appropriate calcined metal oxides, a DMC and calcined MMS-4 ÅK were mixed together in desired quantities. Water (20 ml) was added to this physical mixture to make a paste. The paste was extruded and dried at 100° C. for 24 h and then at 170° C. for 5 h to a constant weight yielding catalysts C-IX to C-XXI, respectively. Compositions of catalysts C-IX to C-XXI are reported in Table 2.

TABLE 2

| Catalyst | DMC (g) | $Al_2O_3$ (g) | $TiO_2$ (g) | ZnO (g) | MMS-4ÅK (g) | Yield (g) |
|---|---|---|---|---|---|---|
| C-XIX   | C-XVI (1.5)   | 0.75 | 1.5 | —   | 7.5  | 11.0 |
| C-XX    | C-XVII (3.0)  | 1.5  | 3.0 | —   | 15.0 | 23.0 |
| C-XXI   | C-XVIII (1.5) | 0.75 | 1.5 | —   | 7.5  | 11.3 |
| C-XXIII | C-XXII (5.0)  | 3.0  | 5.0 | 5.0 | 18   | 36.0 |

Preparation of Catalyst C-XXII

DMC catalyst C-XXII having molecular formula $Fe_2Zn_3(CN)_{10}$ was prepared using hexacyanoferrate(II)-trihydrate (7.4 g) and Zinc chloride (23.9 g) following literature-described methods.

Reaction—Examples

Batch Process for Transesterification of Canola Oil to Biodiesel

With respect to Table 3 below, a solid, mixed catalyst was placed with a mixture of 10 g canola oil and 65 ml methanol in a 100 ml stainless steel autoclave equipped with a pressure gauge and pressure relief valve. The autoclave was sealed and heater in an oil bath at 200° C.±10° C. After cooling and release of pressure, the catalyst was recovered from the reaction products and washed with methanol prior to reuse (and reactivated, if necessary). The filtrate, containing fatty acid methyl ester (FAME), glycerol, unreacted oil (if any) and methanol, was separated by evaporation and layer separation. Recovered methanol was recycled, glycerol removed, and the remaining oily products were analyzed. The results are presented in Table 3.

TABLE 3

Transesterification of canola oil using batch process

| Catalyst* | % Catalyst $\left(\dfrac{\text{Catalyst (g)} \times 100}{\text{Oil (g)}}\right)$ | Time (h) | % Conversion based on Triglyceride consumption | |
|---|---|---|---|---|
| | | | $1^{st}$ Use | $2^{nd}$ Use |
| ZnO       | 5.0  | 1.5 | 92.2 |      |
| $Al_2O_3$ | 5.0  | 1.5 | 90.4 | 34.0 |
| $TiO_2$   | 5.0  | 1.5 | 30.4 | 20.0 |
| Ms-4ÅK    | 5.0  | 1.5 | 94.8 | 80.0 |
| $La_2O_3$ | 5.0  | 1.5 | 100  | 100  |
| $La_2O_3$ | 16.0 | 1.0 | 100  | 100  |
| C-II      | 5.0  | 1.5 | 100  | 100  |
| C-III     | 5.0  | 1.5 | 100  | 100  |

TABLE 3-continued

Transesterification of canola oil using batch process

| Catalyst* | % Catalyst $\left(\frac{\text{Catalyst (g)} \times 100}{\text{Oil (g)}}\right)$ | Time (h) | % Conversion based on Triglyceride consumption | |
|---|---|---|---|---|
| | | | $1^{st}$ Use | $2^{nd}$ Use |
| C-IV | 5.0 | 1.5 | 100 | 100 |
| C-V | 5.0 | 1.5 | 97.4 | 100 |
| C-VI | 5.0 | 1.5 | 100 | 100 |
| C-VII | 5.0 | 1.5 | 95.6 | 62.6 |
| C-VIII | 10.0 | 1.5 | 100 | 100 |
| C-VIII | 5.0 | 1.5 | 100 | 100 |
| C-IX | 5.0 | 1.5 | 98.3 | 83.5 |
| C-IX | 16.0 | 1.0 | 90.4 | 93.8 |
| C-X | 5.0 | 1.5 | 100 | 100 |
| C-X | 3.0 | 1.5 | 100 | 100 |
| C-X | 16.0 | 1.0 | 100 | 100 |
| C-XI | 5.0 | 1.5 | 100 | 98.3 |
| C-XII | 5.0 | 1.5 | 71.3 | 48.7 |
| C-XII | 16.0 | 1.0 | 82.6 | 82.6 |
| C-XIII | 5.0 | 1.5 | 100 | 100 |
| C-XIII | 16.0 | 1.0 | 100 | 98.3 |
| C-XIV | 5.0 | 1.5 | 67.8 | 58.3 |
| C-XIV | 16.0 | 1.0 | 90.2 | 89.8 |
| C-XV | 5.0 | 1.5 | 40.9 | 27.0 |
| C-XV | 16.0 | 2.0 | 100 | 100 |
| C-XVI | 5.0 | 1.5 | 97.4 | 100 |
| C-XVII | 5.0 | 1.5 | 54.8 | 63.5 |
| C-XVIII | 5.0 | 1.5 | 35.7 | 36.5 |
| C-XIX | 5.0 | 1.5 | 94.8 | 81.7 |
| C-XX | 5.0 | 1.5 | 100 | 81.7 |
| C-XXI | 5.0 | 1.5 | 59.1 | 37.4 |
| C-XXIII | 16.0 | 1.0 | 99.0 | 98.0 |
| C-VIII | 10 | 2.0 | 99.9 | 99.8 |

*Single metal oxides were calcined at 600° C. for 3 hrs prior to use

Batch Process for Esterification of Carboxylic Acids or Free Fatty Acids

With respect to Table 4 below, a mixture of a carboxylic acid or free fatty acids, and appropriate alcohol or phenol, and a catalyst was placed in a 100 ml stainless steel autoclave equipped with a pressure gauge and pressure relief valve. The autoclave was then sealed and heated in an oil bath for the time indicated, then cooled to ambient temperature and pressure released. The reaction material was filtered to recover the catalyst, followed by washing of the catalyst in methanol and reactivation, if necessary. Methanol was removed by evaporation and the residue was washed with bicarbonate solution to remove unreacted acid. Remaining solvent was removed by evaporation, and the recovered ester was analyzed by NMR and GC, with results shown in Table 4.

TABLE 4

Esterification of carboxylic acids

| Sr. No | Carboxylic Acid | ROH | Catalyst | Catalyst % | Time (h) | Conversion % |
|---|---|---|---|---|---|---|
| 1 | Free Fatty Acid prepared from Canola oil | Methanol | C-VIII | 10 | 1 | 100 |
| 2 | Benzoic Acid | Methanol | C-X | 10 | 1.5 | 100 |
| 3 | Benzoic Acid | Methanol | C-VIII | 10 | 2 | 100 |
| 3 | 2-Iodo Benzoic Acid | Methanol | C-X | 10 | 1.5 | 100 |
| 4 | 2-Iodo Benzoic Acid | Methanol | C-VIII | 10 | 1.5 | 100 |

Continuous Fixed Bed Reactor Process for Transesterification of Canola Oil

A tubular stainless steel reactor, equipped with pressure regulator, back pressure control valve and thermometer, was filled with the indicated mixed solid catalyst. Canola oil and methanol were introduced at the indicated ratios and flow rates from bottom of the reactor using two high pressure pumps. The reactor was heated externally such that the temperature inside of the reactor was maintained between 200 and 250° C., and internal pressure was maintained between 350 to 1,000 psi, preferably between 400 to 650 psi. Hot effluents exiting from top of the reactor were flashed into an expansion chamber where methanol vapours were separated, condensed and recycled. Residue liquid was drained into a settling chamber where the lower layer (containing glycerol) was separated from the product. A series of continuous reactions were conducted to optimize feed rate, temperature, pressure and contact time for maximizing the conversion of oil into FAME and improving colour and quality of glycerol. The separated upper layer containing largely the biodiesel product was analysed using NMR and GC to quantify FAME yield and remaining oil if any. Results of runs using different catalysts are reported in Table-5.

TABLE 5

Fixed Bed Transesterification of Canola Oil

| CATALYST | TEMP ° C. | VVH | R H/A VOL/VOL | PRESSURE PSI | CONTACT TIME (MIN) | CONVERSION (%) |
|---|---|---|---|---|---|---|
| C-VIII | 200 | 0.5 | 1.0 | 650 | 60 | 99.8 |
| C-VIII* | 200 | 0.5 | 1.0 | 650 | 60 | 99.8 |
| C-VIII | 200 | 0.5 | 2.0 | 650 | 40 | 98.0 |
| C-VIII | 200 | 1.0 | 1.0 | 650 | 30 | 92.5 |
| C-VIII | 200 | 1.0 | 0.5 | 650 | 40 | 95.0 |
| C-VIII | 200 | 0.75 | 0.5 | 650 | 60 | 98.3 |
| C-VIII | 230 | 0.75 | 0.5 | 650 | 60 | 99.8 |
| C-VIII | 230 | 0.75 | 0.5 | 700 | 60 | 99.9 |
| C-VIII | 200 | 0.3 | 1.0 | 650 | 100 | 99.9 |
| C-VIII | 200 | 0.25 | 1.0 | 650 | 120 | 99.9 |
| C-VIII | 200 | 1.5 | 1.0 | 650 | 40 | 95.0 |
| C-VIII | 215 | 1.5 | 1.0 | 650 | 40 | 97.0 |
| C-VIII | 200 | 2.0 | 1.0 | 650 | 15 | 80.0 |
| C-VII | 200 | 0.5 | 1.0 | 650 | 60 | 99.8 |
| C-VII | 200 | 0.75 | 0.5 | 650 | 60 | 99.7 |

TABLE 5-continued

Fixed Bed Transesterification of Canola Oil

| CATALYST | TEMP °C. | VVH | R H/A VOL/VOL | PRESSURE PSI | CONTACT TIME (MIN) | CONVERSION (%) |
|---|---|---|---|---|---|---|
| C-XXIII | 200 | 0.5 | 1 | 650 | 60 | 97.0 |
| C-III | 200 | 0.5 | 1 | 650 | 60 | 99.8 |

VVH = Volume of oil injected/volume of catalyst per hr., R is ratio by volume of Oil/alcohol.
*Recalcined catalyst after several uses The fixed bed reactor transesterification process may also be completed in two stages. This was carried out in cases where an incomplete conversion of triglycerides to FAME was noticed, or to increase the shift of reaction equilibrium, bringing the reaction to completion more quickly. The recovered upper layer from the reaction above was diluted with the desired quantity of methanol, and introduced into a second reactor system with conditions similar to that described in Table 5. Effluents were concentrated and glycerol removed. Recovered FAME was analyzed using NMR and GC, with results reported below in Table 6. Catalyst beds were regenerated only if required, by heating at 600° C. for three hours except for catalysts containing DMC, which were heated to 170° C. for five hours.

TABLE 6

Two-Stage Fixed Bed Transesterification of Canola Oil

| VVH Stage-1 | VVH Stage-2 | Temp °C. | Pressure PSI | Contact time Stage-1 | Contact time Stage-2 | Conversion % Stage-1 | Conversion % Stage-2 |
|---|---|---|---|---|---|---|---|
| 2 | 2 | 200 | 650 | 15 | 15 | 80 | 95.8 |
| 1 | 2 | 200 | 650 | 30 | 15 | 82 | 95.8 |
| 2 | 1 | 200 | 650 | 15 | 30 | 80 | 93.3 |
| 1 | 1 | 200 | 650 | 30 | 30 | 82 | 99.9 |

VVH = Volume of oil injected/volume of catalyst per hr., R is ratio by volume of Oil/alcohol.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A method for effecting esterification or transesterification of a starting material, comprising reacting the starting material with an alcohol in the presence of a solid, heterogeneous catalyst, wherein the catalyst comprises at least one modified molecular sieves (MMS) type 3 Å, 4 Å, or 5 Å, and at least one of a metal oxide, composite oxide and/or a combination thereof, said metal oxide is an aluminum oxide, a calcium oxide, a strontium oxide, an iron oxide, a gallium oxide, a hafnium oxide, a lanthanum oxide, a silicon oxide, a titanium oxide, a zinc oxide or a zirconium oxide and/or one double-metal cyanide.

2. The method of claim 1, wherein the starting material comprises an oil.

3. The method of claim 1, wherein the starting material is selected from the group consisting of triglycerides, free fatty acids, and a mixture thereof.

4. The method of claim 1, wherein the starting material comprises carboxylic acid.

5. The method of claim 1, wherein biodiesel or a carboxylic acid ester is produced as a reaction product.

6. The method of claim 1, wherein the method produces glycerol as a reaction product.

7. The method of claim 1, wherein soap is not produced as a byproduct of the reaction.

8. The method of claim 1, wherein the reaction is conducted at temperatures less than 250° C.

9. The method of claim 1, wherein the reaction is conducted at pressures less than 1000 psi.

10. The method of claim 1, wherein the reaction is conducted at pressures less than 2000 psi.

11. The method of claim 1, wherein the reaction is conducted in a batch reactor.

12. The method of claim 1, wherein the reaction is conducted continuously using a fixed bed reactor.

13. The method of claim 1, wherein the reaction is conducted in one or more successive stages.

14. The method of claim 1, wherein the reaction is conducted with a ratio of 0.1-2.0 volumes of injected oil/volume of catalyst per hour.

15. The method of claim 1, wherein the solid, heterogeneous catalyst is in powdered, pelleted, or extruded form.

16. The method of claim 1, wherein said solid, heterogeneous catalyst:
   a) is according to the formula $a(La_2O_3) \cdot x(TiO_2) \cdot y(ZnO) \cdot z(MMS)$, wherein a and x are each 1; y is 1-2, z is 3-4, and wherein MMS is a modified molecular sieve obtained from the type 3 Å, 4 Å, or 5 Å zeolite, having the general formula $K_n Na_{(12-n)}[(AlO_2)_{12}(SiO_2)_{12}] \cdot xH_2O$, $Na_{12}[(AlO_2)_{12}(SiO_2)_{12}] \cdot xH_2O$, or $Ca_n Na_{(12-n)}[(AlO_2)_{12}(SiO_2)_{12}] \cdot xH_2O$, respectively, wherein $x_1$ has a value between 0 to 5 inclusive and n has a value between 1 to 12 inclusive, modified by replacement of at least one sodium ion within an unmodified molecular sieve with at least one metal cation, wherein the MMS has the general formula $K_n Na_{(12-n)}[(AlO_2)_{12}(SiO_2)_{12}] \cdot xH_2O$, $K_m Ca_n Na_{\{12-(m+2n)\}}[(AlO_2)_{12}(SiO_2)_{12}] \cdot xH_2O$, $Cs_n Na_{(12-n)}[(AlO_2)_{12}(SiO_2)_{12}] \cdot xH_2O$, or $Cs_m Ca_n Na_{\{12-(m+2n)\}}[(AlO_2)_{12}(SiO_2)_{12}] \cdot xH_2O$, wherein $x_2$ has a value between 0 to 5 inclusive, and m and n independently have a value between 1 to 12 inclusive;
   b) is according to the formula $(Al_2O_3) \cdot (TiO_2) \cdot (ZnO) \cdot z(MMS)$ wherein z is 1 to 10 and wherein MMS is a modified molecular sieve obtained from the type 3 Å, 4 Å, or 5 Å zeolite, having the general formula $K_n Na_{(12-n)}[(AlO_2)_{12}(SiO_2)_{12}] \cdot xH_2O$, $Na_{12}[(AlO_2)_{12}(SiO_2)_{12}] \cdot xH_2O$, or $Ca_n Na_{(12-n)}[(AlO_2)_{12}(SiO_2)_{12}] \cdot xH_2O$, respectively, wherein $x_1$ has a value between 0 to 5 inclusive and n has a value between 1 to 12 inclusive, modified by replacement of at least one sodium ion within an unmodified molecular sieve with at least one metal cation, wherein the MMS has the general formula $K_n Na_{(12-n)}[(AlO_2)_{12}(SiO_2)_{12}] \cdot xH_2O$, $K_m Ca_n Na_{\{12-(m+2n)\}}[(AlO_2)_{12}(SiO_2)_{12}] \cdot xH_2O$, $Cs_n$ $Na_{(12-n)}[(AlO_2)_{12}(SiO_2)_{12}] \cdot xH_2O$, or $Cs_mCa_nNa_{\{12-(m+2n)\}}[(AlO_2)_{12}(SiO_2)_{12}] \cdot xH_2O$, wherein $x_2$ has a value between 0 to 5 inclusive, and m and n independently have a value between 1 to 12 inclusive; or c) is according to the formula $p(Al_2O_3) \cdot q(TiO_2) \cdot r(ZnO) \cdot z(MMS)$ wherein p, q and r independently have a value between 1 to 3 inclusive and z has a value of 1 to 10, and wherein MMS is a modified molecular sieve obtained from the type 3 Å, 4 Å, or 5 Å zeolite, having the general formula $K_nNa_{(12-n)}[(AlO_2)_{12}(SiO_2)_{12}] \cdot xH_2O$, $Na_{12}[(AlO_2)_{12}]$, $x_1H_2O$, or $Ca_nNa_{(12-n)}[(AlO_2)_{12}(SiO_2)_{12}] \cdot x_1H_2O$, respectively, wherein $x_1$ has a value between 0 to 5 inclusive and n has a value between 1 to 12 inclusive, modified by replacement of at least one sodium ion within an unmodified molecular sieve with at least one metal cation, wherein the MMS has the general formula $K_nNa_{(12-n)}[(AlO_2)_f(SiO_2)_g] \cdot x_2H_2O$, $K_mCa_NNa_{\{12-(m+2n)\}}[(AlO_2)_f(SiO_2)_g] \cdot x_2H_2O$, $Cs_nNa_{(12-n)}[(AlO_2)_f(SiO_2)_g] \cdot x_2H_2O$, or $Cs_mCa_nNa_{\{12-(m+2n)\}}[(AlO_2)_f(SiO_2)_g] \cdot x_2H_2O$, wherein $x_2$ has a value between 0 to 5 inclusive, m and n independently have a value between 1 to 12 inclusive, and f and g independently have a value between 1 to 12 inclusive.

17. The method of claim 1, wherein the catalyst is according to the formula $a(Al_2O_3) \cdot x(La_2O_3 \cdot TiO_2) \cdot y(ZnO) \cdot z(MMS)$, wherein a is 0-1; x is 1-2; y is 0-1; z is 1-3 and wherein MMS is a modified molecular sieve obtained from the type 3 Å, 4 Å, or 5 Å zeolite, having the general formula $K_nNa_{(12-n)}[(AlO_2)_{12}(SiO_2)_{12}] \cdot x_1H_2O$, $Na_{12}[(AlO_2)_{12}(SiO_2)_{12}] \cdot x_1H_2O$, or $Ca_nNa_{(12-n)}[(AlO_2)_{12}(SiO_2)_{12}] \cdot x_1H_2O$, respectively, wherein $x_1$ has a value between 0 to 5 inclusive and n has a value between 1 to 12 inclusive, modified by replacement of at least one sodium ion within an unmodified molecular sieve with at least one metal cation, wherein the MMS has the general formula $K_nNa_{(12-n)}[(AlO_2)_{12}(SiO_2)_{12}] \cdot x_2H_2O$, $K_mCa_nNa_{\{12-(m+2n)\}}[(AlO_2)_{12}(SiO_2)_{12}] \cdot x_2H_2O$, $Cs_nNa_{(12-n)}[(AlO_2)_{12}(SiO_2)_{12}] \cdot x_2H_2O$, or $Cs_mCa_nNa_{\{12-(m+2n)\}}[(AlO_2)_{12}(SiO_2)_{12}] \cdot x_2H_2O$, wherein $x_2$ has a value between 0 to 5 inclusive, and m and n independently have a value between 1 to 12 inclusive.

18. The method of claim 1, wherein the catalyst is according to the formula $a(Al_2O_3) \cdot b(TiO_2) \cdot c(ZnO) \cdot d(Fe_2M_x(CN)_{10}) \cdot z(MMS)$, wherein a is 1; b is 0-2; c is 0-2; d is 1-2; x is 2 or 3; z is 1-10, and wherein M is lanthanum, zinc, copper or aluminum; MMS is a modified molecular sieve obtained from the type 3 Å, 4 Å, or 5 Å zeolite, having the general formula $K_nNa_{(12-n)}[(AlO_2)_{12}(SiO_2)_{12}] \cdot x_1H_2O$, $Na_{12}[(AlO_2)_{12}(SiO_2)_{12}] \cdot x_1H_2O$, or $Ca_nNa_{(12-n)}[(AlO_2)_{12}(SiO_2)_{12}] \cdot x_1H_2O$, respectively, wherein $x_1$ has a value between 0 to 5 inclusive and n has a value between 1 to 12 inclusive, modified by replacement of at least one sodium ion within an unmodified molecular sieve with at least one metal cation, wherein the MMS has the general formula $K_nNa_{(12-n)}[(AlO_2)_{12}(SiO_2)_{12}] \cdot x_2H_2O$, $K_mCa_nNa_{\{12-(m+2n)\}}[(AlO_2)_{12}(SiO_2)_{12}] \cdot x_2H_2O$, $Cs_nNa_{(12-n)}[(AlO_2)_{12}(SiO_2)_{12}] \cdot x_2H_2O$, or $Cs_mCa_nNa_{\{12-(m+2n)\}}[(AlO_2)_{12}(SiO_2)_{12}] \cdot x_2H_2O$, wherein $x_2$ has a value between 0 to 5 inclusive, and m and n independently have a value between 1 to 12 inclusive.

* * * * *